United States Patent [19]

Haase et al.

[11] 4,353,840

[45] Oct. 12, 1982

[54] USE OF AMINE-ALUMINUM CHLORIDE ADDUCTS AS ALKYLATION INHIBITORS IN A LIGAND-COMPLEXING PROCESS

[75] Inventors: Donald J. Haase, Houston; David G. Walker, Baytown; Paul C. Ostrowski, Webster, all of Tex.

[73] Assignee: Tenneco Chemicals, Inc., Piscataway, N.J.

[21] Appl. No.: 241,200

[22] Filed: Mar. 6, 1981

Related U.S. Application Data

[62] Division of Ser. No. 171,630, Jul. 23, 1980, abandoned.

[51] Int. Cl.$^3$ .............................................. C07F 5/06
[52] U.S. Cl. .............................. 260/448 R; 260/438.1; 546/9; 585/838; 585/840; 585/848; 585/852
[58] Field of Search ....................... 585/838, 840, 848; 260/438.1, 448 R; 546/9

[56] References Cited

U.S. PATENT DOCUMENTS

| | | | |
|---|---|---|---|
| 3,592,865 | 7/1971 | Long et al. | 260/438.1 |
| 3,647,843 | 3/1972 | Walker et al. | 260/438.1 |
| 3,651,159 | 3/1972 | Long et al. | 585/848 |
| 3,927,176 | 12/1975 | Turnbo et al. | 585/848 |
| 3,933,878 | 1/1976 | Tyler et al. | 585/848 |
| 3,960,910 | 6/1976 | Sudduth et al. | 585/848 |
| 4,014,950 | 3/1977 | Keyworth et al. | 585/840 |
| 4,066,679 | 1/1978 | Long et al. | 260/438.1 |

OTHER PUBLICATIONS

Thomas, Anhydrous Aluminum Chloride in Org. Chem., Reinhold Publ. Corp., N.Y., pp. 19, 36, 53, 74, 156, 157 (1941).
The Chemical Elements and Their Compounds, Oxford Univ. Press, London, vol. 1, pp. 430 (1950).

*Primary Examiner*—Helen M. S. Sneed
*Attorney, Agent, or Firm*—Evelyn Berlow

[57] ABSTRACT

In processes in which liquid sorbents that are solutions in an aromatic hydrocarbon or halogenated aromatic hydrocarbon of a bimetallic salt complex having the generic formula $M_I M_{II} X_n$·Aromatic, wherein $M_I$ is a Group I-B metal, $M_{II}$ is a Group III-A metal, X is halogen, n is the sum of the valences of $M_I$ and $M_{II}$, and Aromatic is a monocyclic aromatic hydrocarbon or halogenated aromatic hydrocarbon are used to separate complexible ligands from a gas feedstream that comprises an olefin having 2 or 3 carbon atoms, alkylation of the aromatic hydrocarbon or halogenated aromatic hydrocarbon is inhibited by incorporating in the liquid sorbent from 8.5 mole percent to 30 mole percent, based on the Group I-B metal in the liquid sorbent, of an amine-aluminum chloride adduct, such as ammonia-aluminum chloride adduct or pyridine-aluminum chloride adduct.

7 Claims, No Drawings

USE OF AMINE-ALUMINUM CHLORIDE ADDUCTS AS ALKYLATION INHIBITORS IN A LIGAND-COMPLEXING PROCESS

This is a division of our copending application Ser. No. 171,630, which was filed on July 23, 1980, now abandoned.

This invention relates to an improved process for the separation of complexible ligands from gas feedstreams that utilizes complexing of the ligands with liquid sorbents that are solutions of bimetallic salt complexes having the generic formula $M_I M_{II} X_n$.Aromatic, wherein $M_I$ is a Group I-B metal, $M_{II}$ is a Group III-A metal, X is halogen, n is the sum of the valences of $M_I$ and $M_{II}$, and Aromatic is a monocyclic aromatic hydrocarbon or halogenated aromatic hydrocarbon having 6 to 12 carbon atoms. The improvement comprises the inclusion in the liquid sorbent of an amount of an amine-aluminum chloride adduct that will inhibit the alkylation of the aromatic component of the sorbent by the lower olefins that are present in the gas feedstream.

Bimetallic salt complexes that have the generic formula $M_I M_{II} X_n$.Aromatic are known to be useful in the separation from gas mixtures of such complexible ligands as olefins, acetylenes, aromatics, and carbon monoxide. For example, in U.S. Pat. No. 3,651,159, Long et al. disclosed a process in which a sorbent solution of cuprous aluminum tetrahalide in toluene was used to separate ethylene, propylene, and other complexible ligands from a gas feedstream. The complexed ligands were recovered by ligand exchange with toluene. The resulting solution of cuprous aluminum tetrahalide.toluene in toluene was recycled and used to separate additional quantities of the complexible ligand from the gas feedstream. Walker et al. in U.S. Pat. No. 3,647,843 disclosed a process in which a hydrocarbon pyrolysis gas feedstream was contacted with a cuprous aluminum tetrachloride solution in toluene to separate acetylene from the gas feedstream as a solution of the complex $HC\equiv CH.CuAlCl_4$ in toluene. Acetylene was stripped from this complex, and the cuprous aluminum tetrachloride.toluene solution was recycled.

In processes such as those disclosed by Long et al. and by Walker et al. in which a liquid sorbent containing a bimetallic salt complex is recycled without purification and is used for long periods of time, there is a gradual increase in the amounts of reaction by-products and other impurities in it until sufficient impurities are present to interfere with the efficient operation of the process. For example, when the liquid sorbent is contacted with a gas stream that contains ethylene and/or propylene, some of the olefin reacts with the aromatic hydrocarbon or halogenated aromatic hydrocarbon in the sorbent to form alkylated aromatic compounds and some undergoes polymerization to form olefin oligomers. These reactions are catalyzed by hydrogen chloride or other acidic compounds that are in the gas feedstream or are formed as by-products of the reaction between the liquid sorbent and trace amounts of water or certain other impurities in the gas feedstream.

In ligand separation processes that involve the complexing of ligands with a liquid sorbent that is a solution of a bimetallic salt complex in an aromatic hydrocarbon, it is necessary to minimize the formation of alkylated aromatic compounds because the presence of these compounds not only adversely affects the complexing ability of the liquid sorbent but also leads to corrosion of the processing equipment and to deposition of copper on the surfaces of the processing equipment.

A number of procedures have been proposed in the prior art for inhibiting the reactions between the liquid sorbent and lower olefins to form alkylated aromatic compounds and olefin oligomers by removing or neutralizing the acidic materials that catalyze these reactions, but none has proven to be entirely satisfactory. Some of these procedures fail to reduce the amounts of reaction by-products to the desired very low levels, while others interfere with the efficient operation of the ligand-separation process. For example, Long et al. in U.S. Pat. No. 3,651,195, No. 3,887,600, No. 4,066,679, and No. 4,141,960 disclosed the use of a very small amount of a neutralizing agent, such as ammonia or an organic nitrogen compound, to reduce the residual catalytic activity or acidity of the system. They taught that the amount of neutralizing agent should be merely enough to react with the free acidity of the system because larger amounts of the neutralizing agent will cause precipitation of the copper salt from the solution and lead to the formation of different catalytic species. They preferred to use from 0.01 to 1 wt. percent, based on the liquid sorbent, of the neutralizing agent. Combinations of organic phosphines and organic nitrogen bases were used by Horowitz et al. in U.S. Pat. No. 3,758,609 to inhibit side reactions during olefin-complexing processes in which liquid sorbents containing cuprous aluminum tetrachloride were used as the complexing agent. The useful organic nitrogen bases included substituted pyridines, tertiary alkyl amines, and tertiary alkyl aryl amines. Pyridine was said to be ineffective as an inhibitor because it reacts with the liquid sorbent to form precipitates that contain sizeable amounts of the organic base. According to Keyworth in U.S. Pat. No. 4,014,950, ammonia cannot be used to inhibit the polymerization and alkylation reactions that take place during processes in which liquid sorbents that contain bimetallic salt complexes are used to separate complexible ligands from gas feedstreams. Walker et al. in U.S. Pat. No. 3,845,188 disclosed a process for the recovery of cuprous chloride from spent liquid sorbents that comprise cuprous aluminum tetrachloride by contacting the liquid sorbent with anhydrous ammonia. The cuprous chloride that precipitates quantitatively from the solution is readily separated from the ammonia-aluminum chloride adduct that remains in solution. Although aluminum chloride can be recovered from this solution, in most cases the ammonia-aluminum chloride adduct is separated from the toluene and discarded. In U.S. Pat. Nos. 3,755,487 and 3,758,608, soluble compounds of antimony, arsenic, and bismuth, phosphines, amines, and other additives are added to liquid sorbents that comprise cuprous aluminum tetrachloride to minimize side reactions, to reduce the corrosion effect of the cuprous salt solution, and to prevent the deposition of copper from the solution. Tyler et al. in U.S. Pat. Nos. 3,776,972 and 3,933,878 disclosed that trialkyl phosphines and certain other complexible ligands can be used to inhibit alkylation and polymerization side-reactions in olefin-complexing processes employing liquid sorbents that comprise cuprous aluminum tetrachloride and an aromatic hydrocarbon.

In accordance with this invention, it has been found that the alkylation and other side reactions that take place when a gas feedstream that comprises ethylene and/or propylene is contacted with a liquid sorbent that comprises a bimetallic salt complex of the formula $M_I$·$M_{II}X_n$·Aromatic wherein $M_I$ is a Group I-B metal, $M_{II}$ is a Group III-A metal, X is halogen, n is the sum of the valences of $M_I$ and $M_{II}$, and Aromatic is a monocyclic aromatic hydrocarbon or halogenated aromatic hydrocarbon having 6 to 12 carbon atoms, can be substantially reduced by incorporating in the liquid sorbent an inhibiting amount of an amine-aluminum chloride adduct that is at least moderately soluble in the liquid sorbent. The presence of the amine-aluminum chloride adduct in the liquid sorbent makes it possible to reversibly absorb ethylene and/or propylene without encountering appreciable deterioration of the liquid sorbent resulting from reaction between the liquid sorbent and the olefins, thereby lengthening the time that the liquid sorbent can be used without purification in the ligand separation process.

The liquid sorbents that are stabilized by the process of this invention are solutions of a bimetallic salt complex in an aromatic hydrocarbon or a halogenated aromatic hydrocarbon. The bimetallic salt complexes have the generic formula $M_I M_{II} X_n$·Aromatic. $M_I$ is a Group I-B metal, that is, copper, silver or gold. Copper (I) is the preferred metal. $M_{II}$ is a Group III-A metal, that is, boron, aluminum, gallium, indium, or thallium. Boron and aluminum are the preferred metals, aluminum being particularly preferred. X is halogen, i.e., fluorine, chlorine, bromine, or iodine; it is preferably chlorine or bromine. The sum of the valences of $M_I$ and $M_{II}$ is represented by n. Aromatic is a monocyclic aromatic hydrocarbon or halogenated aromatic hydrocarbon having 6 to 12 carbon atoms, and preferably 6 to 9 carbon atoms, such as benzene, toluene, ethylbenzene, xylene, mesitylene, chlorobenzene, bromobenzene, iodobenzene, dichlorobenzene, dibromobenzene, chlorotoluene, bromotoluene, iodotoluene, or chloroxylene. It is preferably benzene or toluene. Illustrative of these bimetallic salt complexes are the following: $CuBF_4$·benzene, $CuBCl_4$·benzene, $AgBF_4$·mesitylene, $AgBCl_4$·xylene, $AgAlCl_4$·xylene, $AgAlBr_4$·bromobenzene, $CuGaCl_4$·toluene, $CuInI_4$·1,2-dichlorobenzene, $CuTl I_4$·p-chlorotoluene, and the like. The preferred bimetallic salt complexes are $CuAlCl_4$·benzene, $CuAlCl_4$·toluene, and $CuAlBr_4$·benzene. The aromatic hydrocarbon or halogenated aromatic hydrocarbon in which the bimetallic salt complex is dissolved is usually and preferably the same as that used in the preparation of the bimetallic salt complex, but if desired it may be a different one. The total amount of aromatic hydrocarbon or halogenated aromatic hydrocarbon in the liquid sorbent, that is, the amount in the bimetallic salt complex plus the amount used as solvent, is at least 10 mole percent of the amount of the bimetallic salt $M_I M_{II} X_n$ that is present. It is preferred that the amount of aromatic hydrocarbon or halogenated aromatic hydrocarbon be 100 to 450 mole percent of the amount of the bimetallic salt. The particularly preferred liquid sorbents contain 25 to 75 percent by weight of $CuAlCl_4$·benzene in benzene or $CuAlCl_4$·toluene in toluene.

In the practice of this invention, a gas feedstream that contains ethylene and/or propylene is contacted with a liquid sorbent that contains an alkylation-inhibiting amount of an amine-aluminum chloride adduct. The ethylene, propylene, and other complexible ligands in the gas feedstream react with the liquid sorbent to form a reaction mixture that comprises complexes of the ligands with the bimetallic salt complex. The reaction mixture is then heated or treated with another complex- ible ligand to displace the olefin and other complexible ligands from it. The liquid sorbent is then recycled and used to separate additional amounts of the ligands from the gas feedstream.

During this process, any water that is in the gas feedstream reacts with the cuprous aluminum tetrachloride or other bimetallic salt complex in the liquid sorbent to form hydrogen chloride, as is shown in the following equations:

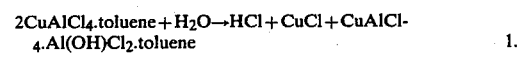   1.

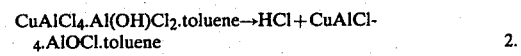   2.

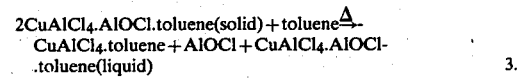   3.

The hydrogen chloride that is formed reacts with the amine-aluminum chloride adduct to form compounds that do not catalyze the alkylation of the aromatic compound in the liquid sorbent. The reaction that takes place between the pyridine-aluminum chloride adduct and hydrogen chloride is shown in the following equation:

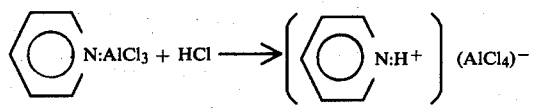

The product of the reaction between the adduct and hydrogen chloride is not an alkylation inhibitor.

The amine-aluminum chloride adducts that are used to inhibit alkylation and other side-reactions in the process of this invention are those that are at least moderately soluble in the liquid sorbent and that react with hydrogen chloride to form sorbent-soluble reaction products. A preferred group of the amine-aluminum chloride adducts have the formula

wherein each R represents hydrogen, alkyl having 1 to 3 carbon atoms, phenyl or alkylphenyl. Illustrative of these adducts are ammonia-aluminum chloride, dimethylamine-aluminum chloride, trimethylamine-aluminum chloride, triethylamine-aluminum chloride, tripropylamine-aluminum chloride, methyldipropylamine-aluminum chloride, aniline-aluminum chloride, methylaniline-aluminum chloride, dimethylaniline-aluminum chloride, diethylaniline-aluminum chloride, methyldiphenylamine-aluminum chloride, and the like. Another preferred group of the amine-aluminum chloride adducts have the formula

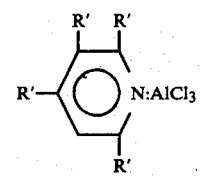

wherein each R' represents hydrogen or alkyl having 1 to 4 carbon atoms. These adducts include pyridine-aluminum chloride, methylpyridine-aluminum chloride, dimethylpyridine-aluminum chloride, trimethylpyridine-aluminum chloride, tetramethylpyridine-aluminum chloride, ethylpyridine-aluminum chloride, isopropylpyridine-aluminum chloride, di-tert.butylpyridine-aluminum chloride, and the like. Either a single amine-aluminum chloride adduct or a mixture of two or more of these adducts can be used in the practice of this invention.

For reasons of economy and efficiency, the preferred amine-aluminum chloride adducts are usually the pyridine-aluminum chloride adduct and the ammonia-aluminum chloride adduct. When relatively large amounts of water, e.g., 100 to 800 ppm, are in the gas feedstream either continuously or intermittently, the most effective alkylation inhibitors are the dimethylaniline-aluminum chloride adduct and the aniline-aluminum chloride adduct.

The amount of the amine-aluminum chloride that is incorporated in the liquid sorbent is at least the amount required to react with the hydrogen chloride and other acidic compounds that are formed when the traces of water and certain other impurities in the gas feedstream react with the bimetallic salt complex in the liquid sorbent. Satisfactory inhibition of alkylation is usually achieved when the liquid sorbent contains at least 8.5 mole percent of the adduct, based on the copper or other Group I-B metal in the bimetallic salt complex in the liquid sorbent. When the gas feedstream contains a relatively large amount of water or certain other impurities, as much as 30 mole percent of the adduct, based on the copper in the liquid sorbent, may be required to inhibit undesirable side reactions during the ligand-separation process. In most cases, from 10 to 20 mole percent of the amine-aluminum chloride adduct, based on the copper in the liquid sorbent, is used to inhibit alkylation.

While all of the amine-aluminum chloride adduct may be added to the liquid sorbent before the sorbent is contacted with the gas feedstream, it is preferred that a minor portion (less than 50%) of the inhibitor be present at the start of the ligand-separation process and that the remainder be added continuously or intermittently during the ligand-separation process at approximately the rate at which the adduct is being removed from the liquid sorbent by reaction with the hydrogen chloride that results from the reaction between the bimetallic salt complex in the liquid sorbent and water in the gas feedstream.

Either an amine-aluminum chloride adduct per se or a solution of an adduct in either liquid sorbent, an aromatic hydrocarbon, or a halogenated aromatic hydrocarbon may be added to the liquid sorbent. The adduct is preferably added to the sorbent as a saturated (1.56 M) solution in toluene or as a saturated solution in a liquid sorbent that comprises cuprous aluminum tetrachloride and an aromatic hydrocarbon.

The amine-aluminum chloride adducts that are used to stabilize the liquid sorbent by inhibiting alkylation of its aromatic component may be prepared by any suitable and convenient procedure. For example, an amine can be reacted with an equivalent amount of aluminum chloride in toluene or another aromatic hydrocarbon to form the adduct. The alkylation inhibitors are preferably prepared by adding to a liquid sorbent that is a solution of cuprous aluminum tetrachloride in an aromatic hydrocarbon from about 15 mole percent to 50 mole percent, based on the copper in the liquid sorbent, of an amine having the formula

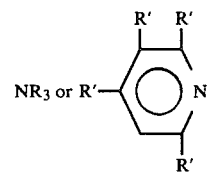

wherein R and R' have the aforementioned significance, maintaining the resulting solution at a temperature in the range of 25° C. to 100° C. until precipitation of cuprous chloride has been completed, and separating the precipitated cuprous salt from a solution of the amine-aluminum chloride adduct and cuprous aluminum tetrachloride in the aromatic hydrocarbon.

Solutions of the amine-aluminum chloride adducts in liquid sorbents that comprise cuprous aluminum tetrachloride and an aromatic hydrocarbon are stable in the presence of oxygen, and they do not deteriorate when they are heated for long periods of time. For example, a liquid sorbent that comprised cuprous aluminum tetrachloride, toluene, and 15 mole percent, based on the copper, of the pyridine-aluminum chloride adduct underwent little decomposition when it was heated at 120°–125° C. for 34 days. During that time, cuprous chloride precipitated at the rate of about 6 percent/year and copper metal precipitated at the rate of about 4 percent/year; there was no detectible formation of tar, methyl group transalkylation, disappearance of pyridine, or change in the ability of the liquid sorbent to form complexes with ethylene and propylene.

This procedure for the stabilization of liquid sorbents by inhibiting alkylation of the aromatic compounds in the sorbent is useful not only in processes in which ethylene and/or propylene is being separated from gas feedstreams but also in those in which carbon monoxide or another complexible ligand is being separated from a gas feedstream that contains trace amounts of the lower olefins as impurities.

The invention is further illustrated by the following examples.

EXAMPLE 1

A. A liquid sorbent was prepared by adding 1.1 moles of cuprous chloride to 1 mole of anhydrous aluminum chloride in toluene. The resulting solution was filtered to remove unreacted cuprous chloride from it and then heated under vacuum to separate toluene and other volatile materials from the cuprous aluminum tetrachloride. The cuprous aluminum tetrachloride was then dissolved in fresh anhydrous toluene to form a liquid sorbent that had a density of 1.26 g./ml.

B. To a portion of the liquid sorbent was added anhydrous pyridine in the amount of 30 mole percent, based on copper in the liquid sorbent. The mixture was stirred at 25° C. until precipitation of cuprous chloride had been completed. A solution of the pyridine-aluminum chloride adduct in the liquid sorbent was separated from the precipitated cuprous chloride.

C. To a liquid sorbent prepared by the procedure of Example 1A was added an amount of a pyridine-aluminum chloride adduct solution prepared by the procedure of Example 1B sufficient to form a liquid sorbent that contained 15 mole percent of the pyridine-aluminum chloride adduct, based on copper in the sorbent. The inhibitor-containing liquid sorbent was heated to 100° C. and 2.50 mmol of propylene was added to it. The sorbent, which contained the propylene-cuprous aluminum tetrachloride complex, was heated at 80° C. for 17 hours and then stripped twice under vacuum at 80° C. The recovered gas contained 88% of the propylene that had been charged.

D. To a liquid sorbent prepared by the procedure of Example 1A was added an amount of a pyridine-aluminum chloride adduct solution prepared by the procedure of Example 1B sufficient to form a liquid sorbent that contained 13.8 mole percent of the adduct, based on copper in the liquid sorbent. The inhibitor-containing liquid sorbent was complexed with 3.5 mmol of propylene and the resulting solution was heated at 80° C. for 165 hours and then stripped twice under vacuum at 80° C. The recovered gas contained 46% of the propylene that had been charged.

During the time that the liquid sorbent that contained the propylene-cuprous aluminum tetrachloride complex was heated at 80° C., propylene disappeared from it at the rate of 0.007 mmol/hour.

E. To a liquid sorbent prepared by the procedure of Example 1A was added an amount of a pyridine-aluminum chloride adduct solution prepared by the procedure of Example 1B sufficient to form a liquid sorbent that contained 13.8 mole percent of the adduct, based on copper in the liquid sorbent. The inhibitor-containing liquid sorbent was complexed with 3.5 mmol of ethylene and the resulting solution was heated at 80° C. for 165 hours and then stripped twice under vacuum at 80° C. The recovered gas contained substantially all of the ethylene that had been charged.

COMPARATIVE EXAMPLE A

The procedure described in Example 1C was repeated except that the liquid sorbent that was contacted with propylene contained 8.4 mole percent of the pyridine-aluminum chloride adduct, based on copper in the sorbent. When the sorbent that contained the propylene-cuprous aluminum tetrachloride complex was stripped twice under vacuum at 80° C., less than 20% of the propylene charged was recovered.

EXAMPLE 2

To a 5 ml. portion of a liquid sorbent prepared by the procedure described in Example 1A, which contained 13.5 mmole of copper, was added a solution of 244 mg. (2.02 mmol) of N,N-dimethylaniline in 2 ml. of anhydrous toluene. The resulting mixture was heated at 80° C. and then filtered to separate precipitated cuprous chloride from the liquid sorbent that contained 17.4 mole percent, based on copper in the sorbent, of the N,N-dimethylaniline-aluminum chloride adduct. This inhibited liquid sorbent was contacted with 5.23 mmol of propylene at 80° C. at an original pressure of 450 torr for 17 hours. The resulting liquid sorbent, which contained the propylene-cuprous aluminum tetrachloride complex, was stripped twice under vacuum at 80° C. to remove 5.60 mmol of propylene from it. When the stripped liquid sorbent was analyzed to determine the amount of alkylation of the toluene that had taken place, the following results were obtained:

| Isopropyl groups | - 0.0117 mmol |
|---|---|
| Ipr/Cu | - 0.0010 |

| -continued | |
|---|---|
| $C_3H_6$/Ipr | - 0.0022 |

From these data, it will be seen that during the process in which propylene was contacted with a liquid sorbent that comprised cuprous aluminum tetrachloride and toluene the alkylation of the toluene was substantially inhibited by the presence of the N,N-dimethylaniline-aluminum chloride adduct in the liquid sorbent.

EXAMPLE 3

To a 5 ml. portion of a liquid sorbent prepared by the procedure described in Example 1A, which contained 12.7 mmol of copper, was added 2.05 mmol of ammonia. The resulting mixture was heated to 75° C. for one hour and then filtered to separate precipitated cuprous chloride from the liquid sorbent that contained 19.1 mole percent of the ammonia-aluminum chloride adduct, based on copper in the liquid sorbent. This liquid sorbent was contacted with 1.30 mmol of propylene at 80° C. at an original pressure of 250 torr for 16 hours. The resulting liquid sorbent, which contained the propylene-curpous aluminum tetrachloride complex, was stripped twice under vacuum at 80° C. to remove 1.25 mmol (96.2% recovery) of propylene from it. The stripped sorbent after hydrolysis contained 0.0197 mmol of isopropyl groups and had an Ipr/Cu ratio of 0.00184 and a $C_3H_6$/Ipr ratio of 0.015.

COMPARATIVE EXAMPLE B

The procedure described in Example 3 was repeated except that the liquid sorbent contained 8 mole percent of the ammonia-aluminum chloride adduct, based on copper in the liquid sorbent. When the liquid sorbent, which contained the propylene-cuprous aluminum tetrachloride complex, was stripped twice under vacuum at 80° C., only 6.3% of the propylene was recovered. The remainder of the propylene had reacted with the toluene in the liquid sorbent to form isopropyltoluenes.

EXAMPLE 4

When the procedure described in Example 3 was repeated except that a saturated solution of the ammonia-aluminum chloride adduct in benzene was added to a liquid sorbent that was a solution of cuprous aluminum tetrachloride in benzene, similar results were obtained.

EXAMPLE 5

When the procedure described in Example 3 was repeated except that the inhibited liquid sorbent was contacted with ethylene and then stripped under vacuum at 80° C., there was quantitative recovery of the ethylene from the inhibited liquid sorbent.

EXAMPLE 6

To a 5 ml. portion of a liquid sorbent prepared by the procedure described in Example 1A, which contained 13.5 mmol of copper, was added a solution of 217.6 mg (2.02 mmol) of triethylamine in 2 ml. of anhydrous toluene. The reaction mixture was heated at 85° C. for 4 hours and then filtered to separate precipitated cuprous chloride from the liquid sorbent that contained 18.9 mole percent of triethylamine-aluminum chloride adduct, based on copper in the liquid sorbent. This inhibited liquid sorbent was contacted with 5.23 mmol of propylene at 80° C. at an original pressure of 450 torr for 17 hours. The resulting liquid sorbent, which contained the propylene-cuprous aluminum tetrachloride complex, was stripped twice under vacuum at 80° C. to remove 5.43 mmol of propylene from it. The stripped sorbent after hydrolysis contained 0.172 mmol of isopropyl groups and had an Ipr/Cu ratio of 0.0151 and a $C_3H_6$Ipr ratio of 0.0329.

EXAMPLE 7

The procedure described in Example 6 was repeated except that the liquid sorbent that was contacted with propylene contained 15 mole percent of 2,4,6-trimethylpyridine-aluminum chloride adduct, based on copper in the liquid sorbent. When the sorbent that contained the propylene-cuprous aluminum tetrachloride complex was stripped twice at 80° C. under vacuum, 92.7% of the propylene was recovered.

EXAMPLE 8

A. To a 5 ml. portion of a liquid sorbent prepared by the procedure of Example 1A that contained 12.9 mole percent of the pyridine-aluminum chloride adduct, based on copper in the liquid sorbent, was added 3.43 mmol of propylene. After 2 hours at 80° C., the reaction mixture was stripped under vacuum. The 3.19 mmol of gas that was recovered contained 96.2% propylene, 3.5% propane, and 0.4% ethane.

B. The residual liquid sorbent was complexed with 3.77 mmol of propylene at 80° C. for 18.2 hours and then stripped under vacuum. The 3.84 mmol of gas that was recovered contained 96.5% propylene, 3.0% propane, 0.3% ethane, and 0.3% ethylene.

C. The second residual liquid sorbent was complexed with 4.07 mmol of propylene at 80° C. for 19.5 hours and then stripped under vacuum. The 3.40 mmol of gas that was recovered contained 95.2% propylene, 4.0% propane, 0.5% ethane, and 0.3% ethylene.

D. The third residual liquid sorbent was complexed with 3.33 mmol of propylene at 80° C. for 20.5 hours and then stripped under vacuum. The 2.74 mmol of gas that was recovered contained 95.4% propylene, 4.0% propane, and 0.6% ethane.

EXAMPLE 9

A series of experiments was carried out to determine the effectiveness of various amine-aluminum chloride adducts as alkylation inhibitors in the presence of relatively large amounts of water.

In these experiments, inhibitor-containing liquid sorbents were prepared by adding to 125 ml. portions of a liquid sorbent prepared by the procedure described in Example 1A enough amine so that after precipitation of cuprous chloride the liquid sorbent contained 15 mole percent of the amine-aluminum chloride adduct, based on copper in the sorbent. The liquid sorbents to which amines had been added were heated at 80° C. for three hours and then allowed to stand at room temperature overnight. After centrifugation to remove precipitated cuprous chloride, about 100 ml. of each of the inhibitor-containing liquid sorbents was obtained.

Each of the amine-aluminum chloride adduct-inhibited liquid sorbents was contacted with a gas stream that contained 16.4% of propylene and 800 ppm of water in nitrogen for a period of from 150 minutes to 210 minutes during which samples of the liquid sorbent were removed from the reaction vessel periodically and analyzed to determine the amount of alkylation that the toluene in the liquid sorbent had undergone. The amine-aluminum chloride adducts that were used as alkylation inhibitors and the results obtained are shown in Table I.

From the data in Table I, it will be seen that all of the amine-aluminum chloride adducts evaluated acted as alkylation inhibitors even in the presence of a relatively large amount of water (800 ppm). Particularly good results were obtained when the inhibitor was the N,N-dimethylaniline-aluminum chloride adduct or the aniline-aluminum chloride adduct.

TABLE I

| Inhibitor | Triethylamine-AlCl₃ Adduct | | Pyridine-AlCl₃ Adduct | | Ammonia-AlCl₃ Adduct | | Aniline-AlCl₃ Adduct | | N,N-Dimethyl-aniline-AlCl₃ Adduct | | None | |
|---|---|---|---|---|---|---|---|---|---|---|---|---|
| Cu present at start of test (mmol) | 213 | | 201 | | 243 | | 222 | | 193 | | 254 | |
| C₃H₆ Feed (mmol/min) | 0.359 | | 0.384 | | 0.384 | | 0.384 | | 0.384 | | 0.340 | |
| Sample Time (min) | C₃H₆/Cu | iPr/Cu | C₃H₆/Cu | iPr/Cu | C₃H₆/Cu | iPr/Cu | C₃H₆/Cu | iPr/Cu | C₃H₆/Cu | iPr/Cu | C₃H₆/Cu | iPr/Cu |
| 30 | 0.50 | 0.00059 | 0.057 | 0.0001 | 0.047 | 0.00013 | 0.052 | 0.000079 | 0.060 | <0.00005 | 0.0318 | 0.00829 |
| 60 | 0.097 | 0.00500 | 0.115 | 0.00021 | 0.095 | 0.00033 | 0.104 | 0.000079 | 0.120 | <0.00005 | 0.0493 | 0.03168 |
| 90 | 0.142 | 0.01215 | 0.174 | 0.00030 | 0.145 | 0.00021 | 0.158 | 0.00033 | 0.181 | <0.00005 | 0.0610 | 0.06170 |
| 120 | 0.188 | 0.01964 | 0.234 | 0.00032 | 0.194 | 0.00049 | 0.212 | 0.000109 | 0.244 | <0.00005 | 0.0668 | 0.9862 |
| 150 | 0.234 | 0.02825 | 0.294 | 0.00059 | 0.245 | 0.00041 | 0.262 | 0.000125 | 0.306 | <0.00005 | 0.0704 | 0.13804 |
| 180 | 0.279 | 0.03774 | 0.356 | 0.00101 | 0.297 | 0.00054 | 0.323 | 0.000198 | 0.370 | <0.00005 | — | — |
| 210 | — | — | — | — | — | 0.00103 | 0.380 | 0.000254 | — | — | — | — |
| Relative Rate of Alkylation (%) | 6.4 | | 0.224 | | 0.260 | | 0.035 | | <0.026 | | 100 | |
| Alkylation Rate Reduction | 15.6 | | 446 | | 385 | | 2850 | | >3850 | | 1 | |

What is claimed is:

1. An alkylation inhibitor for ligand-separation processes in which a gas feedstream containing a complexible ligand is contacted with a liquid sorbent comprising cuprous aluminum tetrachloride and an aromatic hydrocarbon that is a solution of an amine-aluminum chloride adduct selected from the group consisting of (a) adducts having the formula $R_3N:AlCl_3$, wherein each R represents hydrogen, alkyl having 1 to 3 carbon atoms, phenyl, or methylphenyl;
(b) adducts having the formula

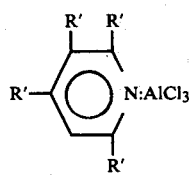

wherein each R' represents hydrogen or alkyl having 1 to 4 carbon atoms, and
(c) mixtures thereof in a solvent selected from the group consisting of aromatic hydrocarbons and liquid sorbents that comprise cuprous aluminum tetrachloride and an aromatic hydrocarbon.

2. An alkylation inhibitor as defined in claim 1 that is a saturated solution of said amine-aluminum chloride adduct in said solvent.

3. An alkylation inhibitor as defined in claim 1 wherein the solvent is toluene.

4. An alkylation inhibitor as defined in claim 1 wherein the solvent comprises cuprous aluminum tetrachloride and toluene.

5. An alkylation inhibitor as defined in claim 1 wherein the amine-aluminum chloride adduct is the ammonia-aluminum chloride adduct.

6. An alkylation inhibitor as defined in claim 1 wherein the amine-aluminum chloride adduct is the pyridine-aluminum chloride adduct.

7. An alkylation inhibitor as defined in claim 1 wherein the amine-aluminum chloride adduct is the N,N-dimethylaniline-aluminum chloride adduct.

* * * * *

UNITED STATES PATENT AND TRADEMARK OFFICE
CERTIFICATE OF CORRECTION

PATENT NO. : 4,353,840

DATED : October 12, 1982

INVENTOR(S) : Donald J. Haase, David G. Walker, and Paul C. Ostrowski

It is certified that error appears in the above-identified patent and that said Letters Patent are hereby corrected as shown below:

Title Page, Item [62], change "abandoned" to -- now U.S. Patent No. 4,317,950 --.

Column 1, line 8, change "abandoned" to -- U.S. Patent No. 4,317,950 --.

Signed and Sealed this

Twenty-first Day of December 1982

[SEAL]

Attest:

GERALD J. MOSSINGHOFF

Attesting Officer

Commissioner of Patents and Trademarks